(12) United States Patent
Crumbley et al.

(10) Patent No.: US 12,703,705 B1
(45) Date of Patent: Aug. 11, 2026

(54) SYSTEM AND METHODS FOR SCALABLE MELANIN PURIFICATION

(71) Applicant: U.S. Army Combat Capabilities Development Command, Chemical Biological Center, APG, MD (US)

(72) Inventors: Anna M Crumbley, Abingdon, MD (US); Frank J Kragl, Churchville, MD (US); Phuong Vi Luu Le, Middle River, MD (US); Henry S Gibbons, Bel Air, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 660 days.

(21) Appl. No.: 18/113,027

(22) Filed: Feb. 22, 2023

Related U.S. Application Data

(60) Provisional application No. 63/314,553, filed on Feb. 28, 2022.

(51) Int. Cl.

| | |
|---|---|
| ***B01D 69/02*** | (2006.01) |
| ***B01D 61/00*** | (2006.01) |
| ***B01D 65/02*** | (2006.01) |
| ***C07D 487/06*** | (2006.01) |

(52) U.S. Cl.
CPC ........... *C07D 487/06* (2013.01); *B01D 61/00* (2013.01); *B01D 65/02* (2013.01); *B01D 69/02* (2013.01); *B01D 2313/243* (2013.01); *B01D 2315/10* (2013.01); *B01D 2317/02* (2013.01); *B01D 2325/20* (2013.01)

(58) Field of Classification Search
CPC ........ B01D 61/00; B01D 65/02; B01D 69/02; B01D 2313/243; B01D 2315/10; B01D 2317/02; B01D 2325/20; C07D 487/06
See application file for complete search history.

(56) References Cited

U.S. PATENT DOCUMENTS

2008/0003211 A1* 1/2008 Fogh ........................ A61P 25/28 424/94.6
2010/0190965 A1* 7/2010 Yamaguchi ........ B01D 71/5211 210/96.2

* cited by examiner

*Primary Examiner* — Patrick Orme
(74) *Attorney, Agent, or Firm* — Ulysses John Biffoni

(57) ABSTRACT

Provided are systems and methods for isolating melanins from a medium that include providing tangential filtration of the medium across a membrane with a 300 kilo Dalton or less cutoff. In some aspects, the methods and systems are suitable for large scale preparations due to the inherent established scalability of the unit operations employed herein. The systems and the methods can be utilized to purify melanins from fermented cell medium as well as from lysates generated therefrom.

12 Claims, 2 Drawing Sheets

FIG. 1

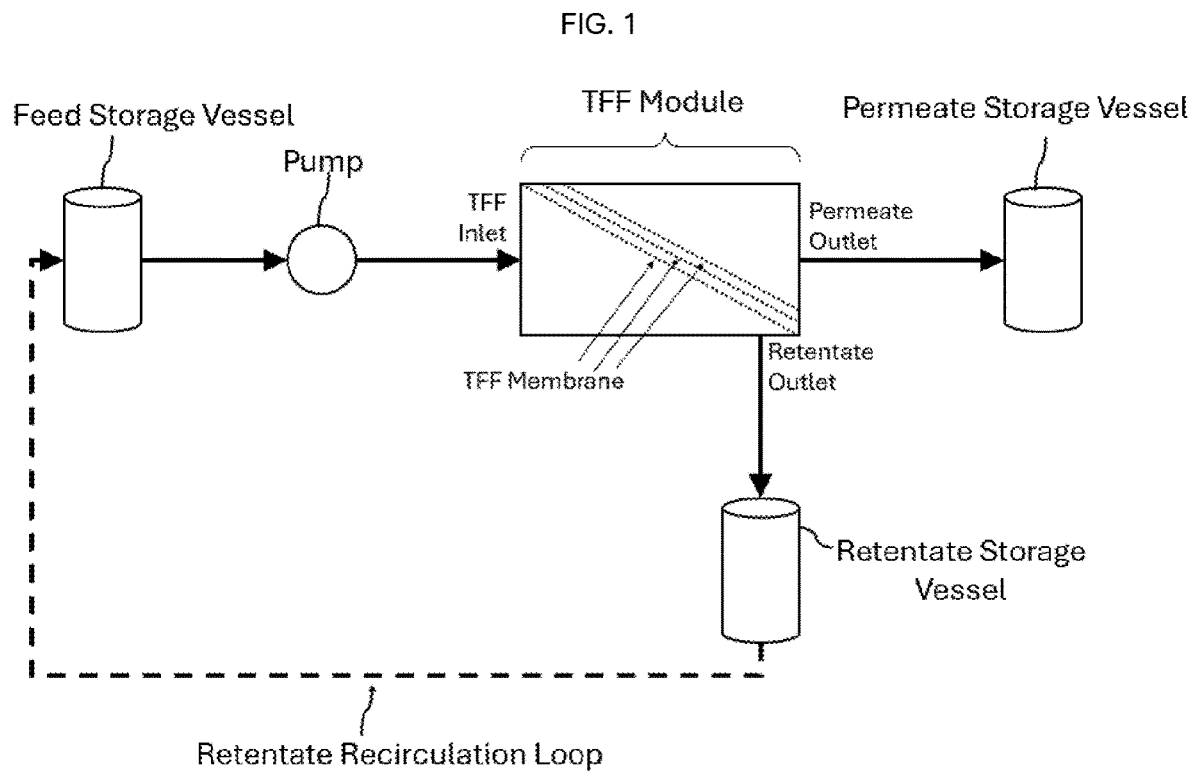

SYSTEM AND METHODS FOR SCALABLE MELANIN PURIFICATION

CROSS-REFERENCE TO RELATED APPLICATIONS

This application claims priority to U.S. Provisional Patent Application 63/314,553, filed Feb. 28, 2022, the contents of which are hereby incorporated by reference in their entirety.

FIELD

The present disclosure is related to systems and methods for the purification and concentration of melanin optionally from microbial cells and cell culture medium.

BACKGROUND

Melanin is an important polymeric material across many industries, including the pharmaceutical, cosmetic, optical, and electronic industries. As melanins are found within many living species, harnessing enzymes that drive their production is an attractive approach to addressing industry demand. The use of microbial organisms offers a relatively inexpensive mechanism by which melanins can be produced on a large scale. Such approaches, however, require isolation and purification of melanin from other cellular materials of the microbes and their extracellular environments. Previous isolation approaches reported in the literature for recovery of melanin produced by microbial fermentation involve the "acid-crash" method, which requires adding hydrochloric acid (HCl) to the solution to a pH<2.0. This requires adding up to 1/10 of the volume 6N HCl, at which point melanin particles independently fall out of solution (see, e.g., journals.asm.org/doi/pdf/10.1128/AEM.02749-19). While this approach is reliable in a laboratory setting, this method does not scale up to industrial levels because of the severe hazards involved and the waste streams created. First, this method calls for liberal use of concentrated hydrochloric acid, a highly corrosive compound that is destructive to stainless steel and is hazardous to the health of operators. Second, use of the previously reported method would result in the generation of large quantities of hazardous waste that would require special disposal. Accordingly, given the industrial demand, a system and method that can provide high quantities of melanins is needed.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

Provided in this disclosure are methods to isolate one or more melanins from an aqueous medium. In some aspects, the methods include providing the aqueous medium to an inlet of a tangential flow filtration (TFF) enclosure at a positive pressure and allowing the aqueous medium to flow across a membrane toward a retentate outlet. Optionally, the membrane has a size restriction of about 300 kilodaltons (kDa) or less and is operably connected to a container for collecting permeate.

In some aspects, a pump may be placed in front or upstream of the inlet to provide the positive pressure. Optionally, the positive pressure is of about 1 to about 10 pounds per square inch (PSI).

In some aspects, the outlet is operably connected to the inlet to allow the aqueous medium to recirculate through the TFF enclosure. Optionally, the inlet is operably connected to a storage container. In further aspects, the outlet optionally leads to the storage container.

The methods as provided herein may further include one or more additional membranes fluidly connected to the membrane, the additional membranes may be downstream to further restrict the mass or size that can permeate through.

The aqueous medium optionally includes or is a fermentation broth. In some aspects, the aqueous medium includes cellular lysate. Optionally, the cellular lysate may be pretreated with at least one of a DNAse, a RNAse, or a proteinase.

In some aspects, the methods may further include drying collected permeate.

The methods as provided herein may further include cleaning the TFF enclosure with water prior to providing the aqueous medium.

Also provided in this disclosure are systems for isolating melanin from an aqueous medium. In some aspects, the system includes a storage container of the aqueous medium operably connected to an inlet of a TFF enclosure, a retentate container operably connected to an outlet of the TFF enclosure, a membrane within the TFF enclosure with a size cut-off of about 300 kDa or less and a permeate container operably connected to the TFF enclosure to collect permeate therefrom.

In some aspects, the membrane is fluidly connected to one or more smaller downstream membranes. In some aspects, a pump is placed prior to the inlet to provide a positive pressure for the aqueous medium within the TFF enclosure. In some aspects, the retentate container is operably connected to the storage container to allow retentate to recirculate through the TFF enclosure.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings FIG. 1 shows an image of workflow setup where the feed solution tube is fed from storage vessel across the pump, which generates a pressure-driven feed into the filter housing.

DETAILED DESCRIPTION

Figure 2:
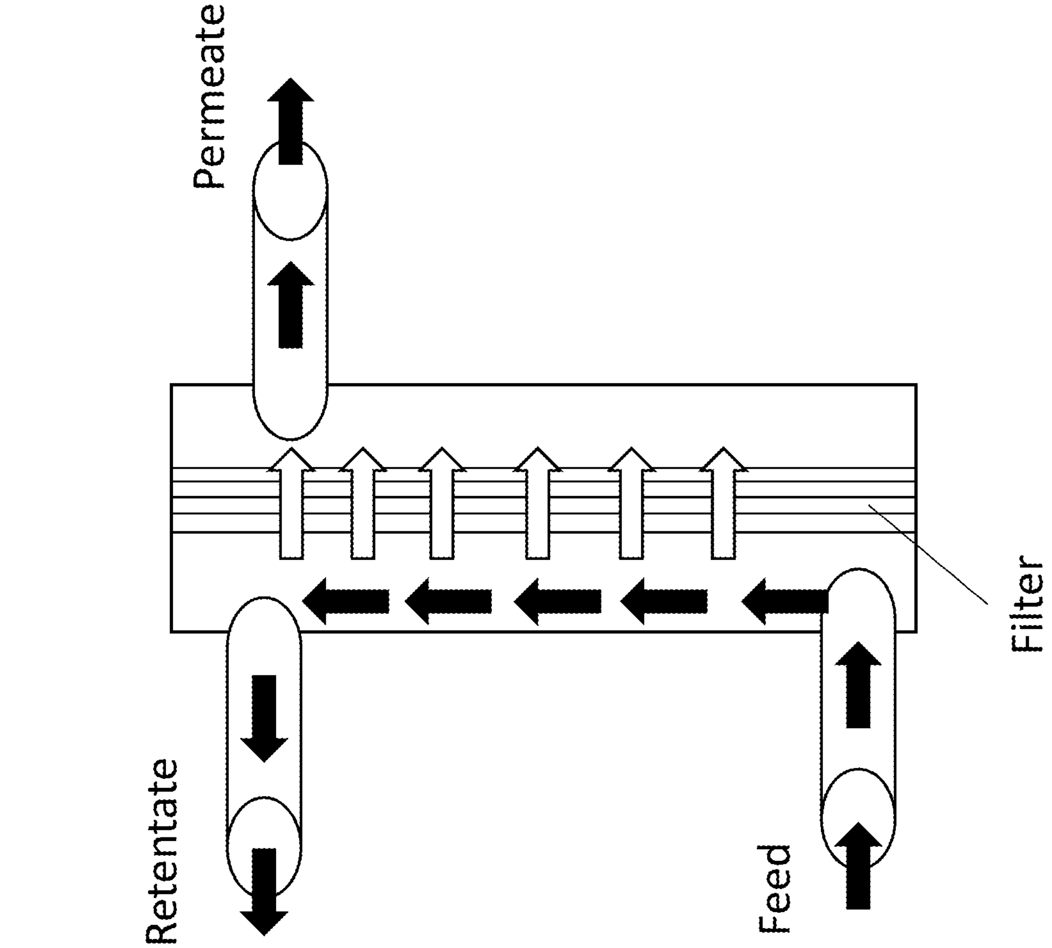
FIG. 2 shows a diagram of the internal flow path for liquids in a TFF membrane configuration.

Provided in this disclosure are systems and methods for purifying and/or isolating melanins from aqueous medium, such as, but not limited to fermented microbe cultures. In some aspects, the systems and methods include providing an aqueous medium with one or more melanins therein in a tangential flow across a membrane.

The systems and methods of the present disclosure include a tangential flow filtration (TFF) arrangement including an enclosure with an inlet feed and a retentate outlet. The TFF enclosure is configured such that as medium enters through the inlet it will naturally progress or flow towards the outlet. As medium passes through the system, it flows across the surface of a membrane to allow for tangential filtration. In some aspects, the TFF enclosure is configured such that medium will flow continuously across a face of a membrane until it reaches the outlet or tube or chamber fluidly connected thereto. Walls or partitions within the TFF enclosure are optionally present to allow for a medium to flow in a pattern, such as a switchback pattern, across the face of the membrane as it proceeds toward the outlet. By the presence of a patterned flow, the medium can flow for a prolonged period across the membrane, providing the opportunity to increase capture of the desired filtrate. In some aspects, the inlet is on a proximal side of the enclosure and the outlet is on a distal side. In other aspects, the inlet and outlet may be on the same side.

The systems and methods of the present disclosure flow a medium across a membrane substantially tangentially with respect to the face of a membrane, thereby providing a permeate with threshold size or selection of sizes. In some aspects, the TFF enclosure may include multiple membranes arranged such that the permeate from the tangential flow is further filtered by one or more additional pore selection sizes. Optionally, a series of membranes can be utilized to sort or further separate melanins by size. In some aspects, a series of membranes can be arranged such that melanin(s) can be isolated into optionally monomeric units.

The system and methods of the present disclosure include generating a flow of medium through the TFF enclosure, including an inlet to allow for the entry of the medium, an enclosed space within an enclosure that provides for the containment of the medium and tangential contact with the membrane, and an outlet for the retentate from the medium to exit the enclosure. In some aspects, the retentate exiting the outlet can be recycled or reintroduced into the feed such that it can enter again though the inlet or recirculate through the system. In some aspects, the retentate is recycled to a storage vessel from which the feed into the enclosure is provided.

In some aspects, a pump may be included in the system or connected thereto. It will be apparent that the placement of one or more pumps may facilitate the flow rate. In some aspects, the pump is operated to provide a flow rate across the membrane of from about 1.0 to about 10 L/min, including about 1.5, 2.0, 2.5, 3.0, 3.5, 4.0, 4.5, 5.0, 5.5, 6.0, 6.5, 7.0, 7.5, 8.0, 8.5, 9.0, and 9.5 L/min. Optionally, at least one pump may be placed between a storage container for the medium to be fed into the enclosure and the inlet into the enclosure. The pump may be placed in front or upstream of the inlet or receive the direction of flow of the medium prior to entry through the inlet. The pump may direct the flow of medium into the inlet. In some aspects, a pump may increase pressure within the enclosure, optionally above 1 atmosphere, to further encourages permeate to cross the membrane. In some aspects, the pump in place before the inlet will generate a positive pressure to assist the flow through the TFF enclosure. In some aspects, the pump is adjusted to provide a positive pressure of about 1 to about 10 psi, including about 1.5, 2.0. 2.5, 3.0, 3.5, 4.0, 4.5, 5.0, 5.5, 6.0, 6.5, 7.0, 7.5, 8.0, 8.5, 9.0, and 9.5 psi, is present from the flow of the medium.

The systems and the methods of the present disclosure provide the ability to extract melanins from a medium by tangential flow filtration across the face of a membrane. In some aspects, the membrane has a molecular weight cut off that allows for melanins to permeate across. Optionally, the membrane has a molecular weight cut off of about 150 to about 300 kDa (kilo Daltons), including about 175, 200, 225, 250, 275, 300 kDa. Optionally, the membrane has a molecular weight cut off of about 300 kDa.

The system and the methods of the present disclosure utilize as a melanin source a medium that includes one or more melanins therein. A medium is optionally an aqueous medium including predominantly water. The melanin may include eumelanin, pheomelanin, neuromelanin, allomelanin, pyomelanin, or any combination thereof. Optionally, the medium may contain homo- and/or hetero-polymers of melanins. In some aspects, the melanins are dissolved, partially dissolved, and/or suspended within the medium, optionally an aqueous medium. In some aspects, a series of membranes may be arranged such that the system may allow for the further separation of larger melanin polymeric units from smaller melanin polymers and/or monomers. Optionally, membranes with a larger molecular weight cutoff are placed closer to the medium than a membrane with a smaller molecular weight cutoff.

The medium may include a cell medium (e.g. lysate, culture medium, etc) from cultured microbes expressing one or more melanins, such as transgenic microbes designed to produce or overproduce one or more melanins. Transgenic microbes are understood by those skilled in the art and may include expression cassettes or vectors with a promoter (e.g. inducible or constitutively active) operably linked to a gene or nucleic acid that encodes for an enzyme that forms a melanin precursor, such as a tyrosinase. In some aspects, the melanin may be secreted into a liquid cell medium by the microorganisms. Such may further be referred to as a supernatant or fermentation broth. The cell medium can then be collected and provided to the TFF arrangement as described herein to collect the melanins in the permeate. In some aspects, the microbes can be isolated from the cell medium prior to TFF, such as through centrifugation.

In some aspects, following collection of the cell medium the microbes can be returned to fresh cell medium and allowed to continue production of the one or more melanins. In addition or alternatively, the microbial biomass can be harvested and broken open to obtain a cellular lysate or biomass thereof. A cellular lysate may be obtained by either enzymatic or mechanical means, or a combination of both. Optionally, the cellular lysate from the microbes can be provided to the TFF arrangement to collect melanins therein.

It is appreciated that a lysate may be combined with a cell medium prior to introduction to a membrane or in contact with a membrane. Optionally, a lysate can be fed in for TFF after the cell medium and/or using a different filtering system. In some aspects, the supernatant and/or collected lysate or biomass can be pre-filtered prior to entry into the TFF enclosure. In some aspects, the supernatant and/or biomass can be filtered at about 0.2 μm pore size or other appropriate size to remove unwanted cellular material or biomass, or other materials that may detract from obtaining the desired melanins in the TFF.

Microbes may be used to produce or overproduce one or melanins. Such may include introducing one or more genes into a microbe and allowing the microbe to divide and increase in number. Such may also include culturing the microbe at a steady temperature and with sufficient nutrients to allow growth and relevant substrates to allow melanin production. The system and the methods may also include inducing fermentation once a desired number or concentration of microbes is achieved. In some aspects, after fermentation is complete, the cell medium or supernatant can be separated by filtration and/or centrifugation.

The microorganisms used for fermentation may optionally be further harvested or lysed. In such aspects, cellular debris may be isolated and the remaining lysate or biomass is used in the TFF enclosure. In some aspects, the microorganisms may be lysed and directly provided to the TFF enclosure.

It is an aspect of the present disclosure that application of TFF for removing one or more melanins from the medium is scalable without issues of pressure changes or flow, thereby allowing the system to be functional on any scale. In particular, the tangential nature of the flow of medium across the membrane prevents larger molecules from potentially lodging or accumulating around the pores of the membrane. As such, the system and the methods described herein are suitable for both laboratory melanin collection and for industrial-scale melanin collection.

Additional options for the system and the methods of the present disclosure may include cleaning and/or wetting the membrane filter prior to contact with the medium with one or more melanins therein.

The permeate can then optionally be further processed to further purify and/or isolate the melanins therein. For example, as described above, additional filters may be applied to the permeate, such as within the TFF or further on to the permeate. In other aspects, isolated melanins may be dried, such as through spray drying, lyophilization, or evaporation. In addition, water can be removed by filtration using a filter press optionally prior to final drying.

It is also further possible that the fermentation medium and/or cell lysates be additionally treated prior to and/or post filtration through the TFF enclosure to remove or reduce other cellular components, such as nucleotide and proteins, such as through treatment with a proteinase, DNAse, RNAse, and/or other macromolecule-degrading enzymes.

Various aspects of the present disclosure are illustrated by the following non-limiting examples. The examples are for illustrative purposes and are not a limitation on any practice of the present disclosure. It will be understood that variations and modifications can be made without departing from the spirit and scope of the disclosure. A person of ordinary skill in the art readily understands where any required reagents or materials may be obtained.

EXAMPLES

The following include examples of different approaches of retrieving melanin from microbe cultures. First, after completing fermentation (specified for a batch process as being completed when the dissolved oxygen readings approaches 100%), harvest bioreactor contents using either centrifuge or TFF installed with a 0.22 μm membrane. Retain both fractions.

The TFF rig is set up, optionally as illustrated in FIG. 1, with feed vessel (e.g. storage vessel), pump, TFF rig with 300 kDa membrane, permeate collection vessel, and retentate line returning to feed vessel.

Prior to filtration of melanin, the TFF setup is cleaned by flushing with water for 30 minutes. All containers are then emptied all water. The melanin-containing supernatant is then transferred to the feed vessel.

The pump is then to parameters noted in Table I to start operation after which the pump is started. In this example, the membrane area is proportional to the volume being processed, i.e. 0.1 $m^2$ for up to 20 L of liquid, 0.5 $m^2$ for up to 100 L of liquid.

TABLE 1

| Tangential Flow Filtration Parameters | |
|---|---|
| Installed Membrane | 300 kDa (Millipore) |
| Feed flow rate | 6 L/min |
| Feed pressure | 10 psi |
| Retentate pressure | 0 psi |
| Permeate flow | 1.5 L/min |

The volume of medium in the system is allowed to decrease to less than 10% of the original volume, then supernatant is flushed with fresh deionized water until salinity registers 0.00 ppt. Salinity is tracked using a handheld Oakton pocket meter. Once the salinity metric is reached, the feed/retentate vessel contents are concentrated to less than 10% of the volume by continuing to run the pump without adding additional water volume.

Contents of the permeate may then be transferred to a drying apparatus, which could operate by either a) lyophilization, b) oven-drying, c) spray-drying, or some combination thereof. The permeate contents may be dried completely, then packaged for storage.

Melanin can and should also be recovered from a cell biomass expressing or otherwise including such melanin. Recovery of the melanin from cellular biomass may occur as follows:

The biomass fraction may be subjected to lysing of the cells using a three-step method: 1) wash biomass using 10 times the volume of process water or until the salinity registers 0.00 ppt as above, 2) transfer biomass to bioreactor or similar vessel that allows for a) heating of the contents to a reliable 37° C. and b) mixing of the contents using continuous stirring, and 3) add lysozyme at a recommended 100 g/mL concentration for at least thirty (30) minutes.

The melanin-containing biomass may then be transferred to a mechanical lysing apparatus, such as a microfluidizer or automated or manually-powered French press.

After lysing the cells, the melanin-containing lysate may then be to the feed vessel for contact with the membrane.

The volume of medium in the system is allowed to decrease to less than 10% of the original volume, then supernatant is flushed with fresh deionized water until salinity registers 0.00 ppt. Salinity is tracked using a handheld Oakton pocket meter. Once the salinity metric is reached, the feed/retentate vessel contents are concentrated to less than 10% of the volume by continuing to run the pump without adding additional water volume.

Contents of the permeate may then be transferred to a drying apparatus, which could operate by either a) lyophilization, b) oven-drying, c) spray-drying, or some combination thereof. The permeate contents may be dried completely, then packaged for storage.

Various modifications of the present disclosure, in addition to those shown and described herein, will be apparent to those skilled in the art of the above description. Such modifications are also intended to fall within the scope of the appended claims.

It is appreciated that all reagents are obtainable by sources known in the art unless otherwise specified.

It is also to be understood that this disclosure is not limited to the specific aspects and methods described herein, as specific components and/or conditions may, of course, vary. Furthermore, the terminology used herein is used only for the purpose of describing particular aspects of the present disclosure and is not intended to be limiting in any way. It will be also understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein. Similarly, as used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Reference is made in detail to exemplary compositions, aspects and methods of the present disclosure, which constitute the best modes of practicing the disclosure presently known to the inventors. The Figures are not necessarily to scale. However, it is to be understood that the disclosed aspects are merely exemplary of the disclosure that may be embodied in various and alternative forms. Therefore, specific details disclosed herein are not to be interpreted as limiting, but merely as a representative basis for any aspect of the disclosure and/or as a representative basis for teaching one skilled in the art to variously employ the present disclosure.

Patents, publications, and applications mentioned in the specification are indicative of the levels of those skilled in the art to which the disclosure pertains. These patents, publications, and applications are incorporated herein by reference to the same extent as if each individual patent, publication, or application was specifically and individually incorporated herein by reference.

The foregoing description is illustrative of particular embodiments of the disclosure, but is not meant to be a limitation upon the practice thereof. The following claims, including all equivalents thereof, are intended to define the scope of the disclosure.

The invention claimed is:

1. A method to isolate one or more melanins from an aqueous medium, the method comprising:

providing the aqueous medium comprising the one or more melanins therein to an inlet of a tangential flow filtration (TFF) enclosure at a positive pressure, wherein the TFF enclosure comprises a retentate outlet and a permeate outlet; and flowing the aqueous medium across a first membrane within the TFF enclosure toward the retentate outlet, wherein the membrane has a size restriction of about 300 kilo Daltons (kDa) or less to isolate the one or more melanins from the aqueous medium, and wherein the permeate outlet is operably connected to a permeate storage container for collecting permeate.

2. The method of claim 1, wherein a pump is placed in front of the inlet to provide the positive pressure.

3. The method of claim 1, wherein the positive pressure is of about 1 to about 10 pounds per square inch (PSI).

4. The method of claim 1, wherein the retentate outlet is operably connected to the inlet to allow the aqueous medium to recirculate through the TFF enclosure.

5. The method of claim 1, wherein the inlet is operably connected to a retentate storage container.

6. The method of claim 5, wherein the retentate outlet is operably connected to the retentate storage container.

7. The method of claim 1, further comprising one or more additional membranes operably connected to the first membrane.

8. The method of claim 1, wherein the aqueous medium comprises a fermentation broth.

9. The method of claim 1, wherein the aqueous medium comprises cellular lysate.

10. The method of claim 9, wherein the cellular lysate is pretreated with at least one of a DNAse, a RNAse, or a proteinase.

11. The method of claim 1, further comprising drying a permeate collected within the permeate storage container.

12. The method of claim 1, further comprising cleaning the TFF enclosure prior to providing the aqueous medium.

* * * * *